United States Patent
Pizzochero et al.

(10) Patent No.: US 11,491,274 B2
(45) Date of Patent: Nov. 8, 2022

(54) LIQUID MEDICAMENT RESERVOIR EMPTY DETECTION SENSOR AND OCCLUSION SENSOR FOR MEDICAMENT DELIVERY DEVICE

(71) Applicant: Becton, Dickinson and Company, Franklin Lakes, NJ (US)

(72) Inventors: Alessandro E. Pizzochero, Chelmsford, MA (US); J. Richard Gyory, Sudbury, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 353 days.

(21) Appl. No.: 16/554,055

(22) Filed: Aug. 28, 2019

(65) Prior Publication Data

US 2020/0069873 A1 Mar. 5, 2020

Related U.S. Application Data

(60) Provisional application No. 62/725,157, filed on Aug. 30, 2018.

(51) Int. Cl.
*A61M 5/168* (2006.01)

(52) U.S. Cl.
CPC . *A61M 5/1684* (2013.01); *A61M 2005/16863* (2013.01); *A61M 2205/3331* (2013.01); *A61M 2205/3386* (2013.01)

(58) Field of Classification Search
CPC ...... A61M 5/1684; A61M 2005/16863; A61M 2005/16868; A61M 2005/16872; A61M 2205/3386; A61M 2205/3331
See application file for complete search history.

(56) References Cited

U.S. PATENT DOCUMENTS

| | | | |
|---|---|---|---|
| 6,423,035 B1 | 7/2002 | Das et al. | |
| 6,656,148 B2 | 3/2003 | Das et al. | |
| 6,652,488 B1 * | 11/2003 | Cover | A61M 1/774 |
| | | | 604/118 |
| 6,659,980 B2 | 12/2003 | Moberg et al. | |
| 8,378,837 B2 | 2/2013 | Wang et al. | |
| 8,469,942 B2 | 6/2013 | Kow et al. | |
| 8,900,213 B2 | 12/2014 | Pope et al. | |
| 9,731,072 B2 | 8/2017 | Estes | |
| 9,895,490 B2 | 2/2018 | Kow et al. | |
| 9,987,425 B2 | 6/2018 | Alderete et al. | |
| 10,226,573 B2 | 3/2019 | Baek et al. | |
| 2004/0127844 A1 * | 7/2004 | Flaherty | A61M 5/16831 |
| | | | 604/67 |
| 2004/0133166 A1 | 7/2004 | Moberg et al. | |
| 2004/0178255 A1 * | 9/2004 | Eich | A61M 5/24 |
| | | | 235/1 R |

(Continued)

FOREIGN PATENT DOCUMENTS

WO WO-2009158655 A2 12/2009

*Primary Examiner* — James D Ponton
(74) *Attorney, Agent, or Firm* — Dickinson Wright PLLC (57) ABSTRACT

A low medicament sensor for a medicament delivery device having a reservoir, a pump, and a fluid path therebetween for medicament, the sensor including a switch and a snap dome. The snap dome is initially in contact with the switch, in fluid communication with the fluid path, and configured to snap out of contact with the switch when a pressure within the snap dome decreases below a predetermined pressure.

16 Claims, 10 Drawing Sheets

(56) References Cited

U.S. PATENT DOCUMENTS

| | | |
|---|---|---|
| 2005/0011282 A1* | 1/2005 | Voege .................. G01P 13/0013 |
| | | 73/861.44 |
| 2005/0171512 A1 | 8/2005 | Flaherty |
| 2011/0152825 A1* | 6/2011 | Marggi ............. A61M 5/14526 |
| | | 604/500 |
| 2014/0058351 A1 | 2/2014 | Pope et al. |
| 2017/0239415 A1 | 8/2017 | Hwang et al. |
| 2019/0143034 A1 | 5/2019 | Anderson et al. |

* cited by examiner

LIQUID MEDICAMENT RESERVOIR EMPTY DETECTION SENSOR AND OCCLUSION SENSOR FOR MEDICAMENT DELIVERY DEVICE

CROSS-REFERENCE TO RELATED APPLICATION

This application claims priority under 35 USC § 119(e) from U.S. provisional patent application Ser. No. 62/725,157, filed on Aug. 30, 2018, the disclosure of which is incorporated herein by reference in its entirety.

FIELD OF THE INVENTION

The present invention relates to medical devices, and more particularly, to medical devices with a sensor for sensing an empty medicament reservoir and/or a sensor for sensing occlusion.

BACKGROUND OF THE INVENTION

Diabetes is a group of diseases characterized by high levels of blood glucose resulting from the inability of diabetic patients to maintain proper levels of insulin production when required. Diabetes can be dangerous to the affected patient if it is not treated, and it can lead to serious health complications and premature death. However, such complications can be minimized by utilizing one or more treatment options to help control the diabetes and reduce the risk of complications.

The treatment options for diabetic patients include specialized diets, oral medications and/or insulin therapy. The main goal of diabetes treatment is to control the diabetic patient's blood glucose or sugar level. However, maintaining proper diabetes management may be complicated because it has to be balanced with the activities of the diabetic patient. Type 1 diabetes (T1D) patients are required to take insulin (e.g., via injections or infusion) to move glucose from the bloodstream because their bodies generally cannot produce insulin. Type 2 diabetes (T2D) patients generally can produce insulin but their bodies cannot use the insulin properly in order to maintain blood glucose levels within medically acceptable ranges. In contrast to people with T1D, the majority of those with T2D usually do not require daily doses of insulin to survive. Many people are able to manage their condition through a healthy diet and increased physical activity or oral medication. However, if they are unable to regulate their blood glucose levels, they will be prescribed insulin. For example, there are an estimated 6.2 million Type 2 diabetes patients (e.g., in the United States, Western Europe and Canada) taking multiple-daily-injections (MDI) which consist of a 24-hour basal insulin and a short acting rapid insulin that is taken at mealtimes for glycemic management control.

For the treatment of Type 1 diabetes (T1D) and sometimes Type 2 diabetes (T2D), there are two principal methods of daily insulin therapy. In the first method, diabetic patients use syringes or insulin pens to self-inject insulin when needed. This method requires a needle stick for each injection, and the diabetic patient may require three to four injections daily. The syringes and insulin pens that are used to inject insulin are relatively simple to use and cost effective.

Another effective method for insulin therapy and managing diabetes is infusion therapy or infusion pump therapy in which an insulin pump is used. The insulin pump can provide continuous infusion of insulin to a diabetic patient at varying rates in order to more closely match the functions and behavior of a properly operating pancreas of a non-diabetic person that produces the required insulin, and the insulin pump can help the diabetic patient maintain his/her blood glucose level within target ranges based on the diabetic patient's individual needs. Infusion pump therapy requires an infusion cannula, typically in the form of an infusion needle or a flexible catheter, that pierces the diabetic patient's skin and through which infusion of insulin takes place. Infusion pump therapy offers the advantages of continuous infusion of insulin, precision dosing, and programmable delivery schedules.

In infusion therapy, insulin doses are typically administered at a basal rate and in a bolus dose. When insulin is administered at a basal rate, insulin is delivered continuously over 24 hours in order to maintain the diabetic patient's blood glucose levels in a consistent range between meals and rest, typically at nighttime. Insulin pumps may also be capable of programming the basal rate of insulin to vary according to the different times of the day and night. In contrast, a bolus dose is typically administered when a diabetic patient consumes a meal, and generally provides a single additional insulin injection to balance the consumed carbohydrates. Insulin pumps may be configured to enable the diabetic patient to program the volume of the bolus dose in accordance with the size or type of the meal that is consumed by the diabetic patient. In addition, insulin pumps may also be configured to enable the diabetic patient to infuse a correctional or supplemental bolus dose of insulin to compensate for a low blood glucose level at the time when the diabetic patient is calculating the bolus dose for a particular meal that is to be consumed.

Insulin pumps advantageously deliver insulin over time rather than in single injections, typically resulting in less variation within the blood glucose range that is recommended. In addition, insulin pumps may reduce the number of needle sticks which the diabetic patient must endure, and improve diabetes management to enhance the diabetic patient's quality of life. For example, many of the T2D patients who are prescribed insulin therapy can be expected to convert from injections to infusion therapy due to an unmet clinical need for improved control. That is, a significant number of the T2D patients who take multiple-daily-injections (MDI) are not achieving target glucose control or not adhering sufficiently to their prescribed insulin therapy.

To facilitate infusion therapy, there are generally two types of insulin pumps, namely, conventional pumps and patch pumps. Conventional pumps require the use of a disposable component, typically referred to as an infusion set, tubing set or pump set, which conveys the insulin from a reservoir within the pump into the skin of the user. The infusion set consists of a pump connector, a length of tubing, and a hub or base from which a cannula, in the form of a hollow metal infusion needle or flexible plastic catheter, extends. The base typically has an adhesive that retains the base on the skin surface during use. The cannula can be inserted into the skin manually or with the aid of a manual or automatic insertion device. The insertion device may be a separate unit required by the user.

Another type of insulin pump is a patch pump. Unlike a conventional infusion pump and infusion set combination, a patch pump is an integrated device that combines most or all of the fluidic components, including the fluid reservoir, pumping mechanism and mechanism for automatically inserting the cannula, in a single housing which is adhesively attached to an infusion site on the patient's skin, and does not require the use of a separate infusion or tubing set. A patch pump containing insulin adheres to the skin and delivers the insulin over a period of time via an integrated subcutaneous cannula. Such devices are replaced on a frequent basis, such as every three days, when the insulin reservoir is exhausted or complications may otherwise occur, such as occlusion of a fluid path or restriction in the cannula or the infusion site.

It is important to determine when the insulin reservoir is exhausted or when there is an occlusion, so that the patient realizes that they are not receiving a full, intended dose of the medicament, such as insulin.

In conventional systems, a fluid low-volume level or an occlusion in the fluid path may be detected too slowly or not at all in some circumstances, with potentially dangerous consequences for the patient. For instance, if an undetected fluid low-volume level or occlusion occurs during insulin infusion, the patient may not receive a necessary amount of medication to prevent a potentially dangerous hyperglycemic event. Because the delivery of the medication fluid may be vital in delivery of medical service, there is a need for rapid detection of exhaustion of medicament in a reservoir and occlusions in medication delivery systems.

Accordingly, improved flow sensing is needed for accurate detection of exhaustion of medicament in a reservoir and/or occlusions.

SUMMARY OF EMBODIMENT OF THE INVENTION

Accordingly, it is an aspect of the present invention to provide a sensor for accurate detection of exhaustion of medicament in a reservoir and/or occlusions.

The foregoing and/or other aspects of the present invention are achieved by providing a low medicament sensor for a medicament delivery device having a reservoir, a pump, and a fluid path therebetween for medicament, the sensor including a switch and a snap dome. The snap dome is initially in contact with the switch, in fluid communication with the fluid path, and configured to snap out of contact with the switch when a pressure within the snap dome decreases below a predetermined pressure.

The foregoing and/or other aspects of the present invention are also achieved by providing a medicament delivery device, including a reservoir for storing medicament, a pump, a fluid path for the medicament fluidly connecting the reservoir and the pump, a switch, and a snap dome. The snap dome is initially in contact with the switch, in fluid communication with the fluid path, and configured to snap out of contact with the switch when a pressure within the snap dome decreases below a predetermined pressure.

The foregoing and/or other aspects of the present invention are also achieved by providing an occlusion sensor for a medicament delivery device having a pump, a medicament delivery cannula, and a medicament delivery fluid path for medicament fluidly connecting the pump and the cannula, the sensor including a switch and a snap dome. The snap dome is initially out of contact with the switch, in fluid communication with the medicament delivery fluid path, and configured to snap into contact with the switch when a pressure in the fluid path increases above a predetermined pressure.

Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which.

DETAILED DESCRIPTION OF EMBODIMENTS OF THE PRESENT INVENTION

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as "up," "down," "bottom,"

"top," "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges around and including the given value, for example, general tolerances associated with manufacturing, assembly, and use of the described embodiments.

Figure 1:
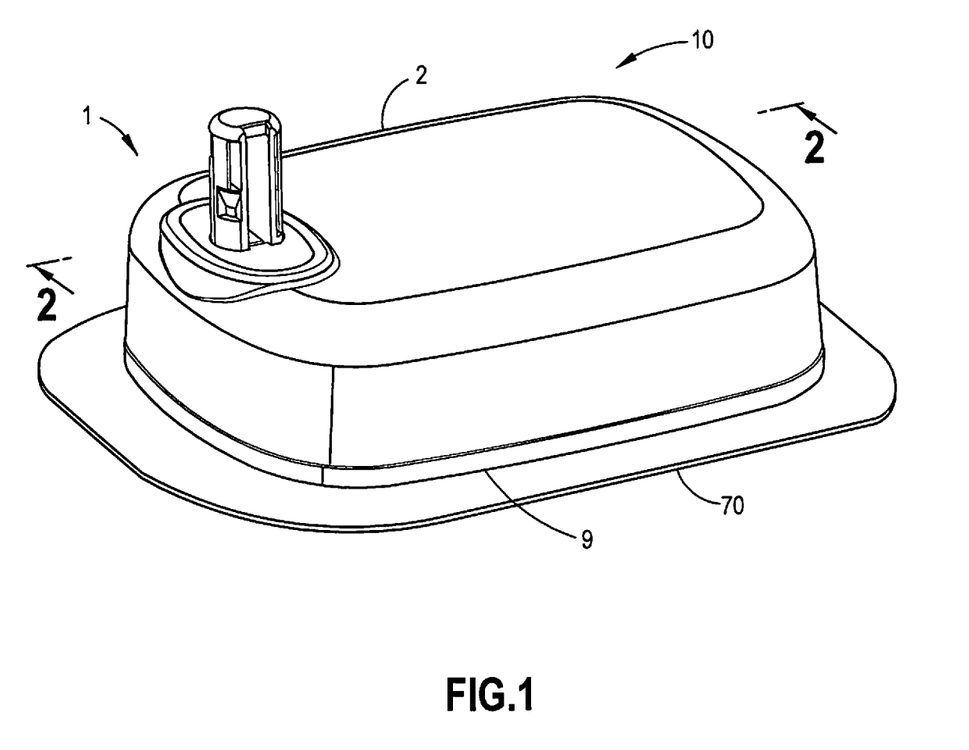
FIG. 1 is a perspective view of a patch pump in accordance with an embodiment of the present invention.

FIG. 1 is a perspective view of a patch pump 1 according to an illustrative embodiment of the present invention. The patch pump 1 has a housing 10, which includes a main cover 2 liquid sealed or, preferably, hermetically sealed to a base 9. The base 9 carries various components as described subsequently. The hermetic seal prevents fluid ingress and prevents other particles from passing the seal. Embodiments of the patch pump 1 also include a vent or a vent membrane along with a sealing method to provide pressure equalization. Embodiments of the seal include, for example, a liquid-tight seal, an O-ring seal or another mechanical seal, a gasket, an elastomer, a heat seal, an ultra-sonically welded seal, a laser weld, chemical joining, an adhesive, a solvent weld, or an adhesive weld. Laser welding is the preferred sealing method because, when laser welding is properly performed, a seamless fully hermetic seal is formed. The vent or the vent membrane continues to have the functional purpose of equalizing internal pressure and providing a sterile environment.

Figure 2:
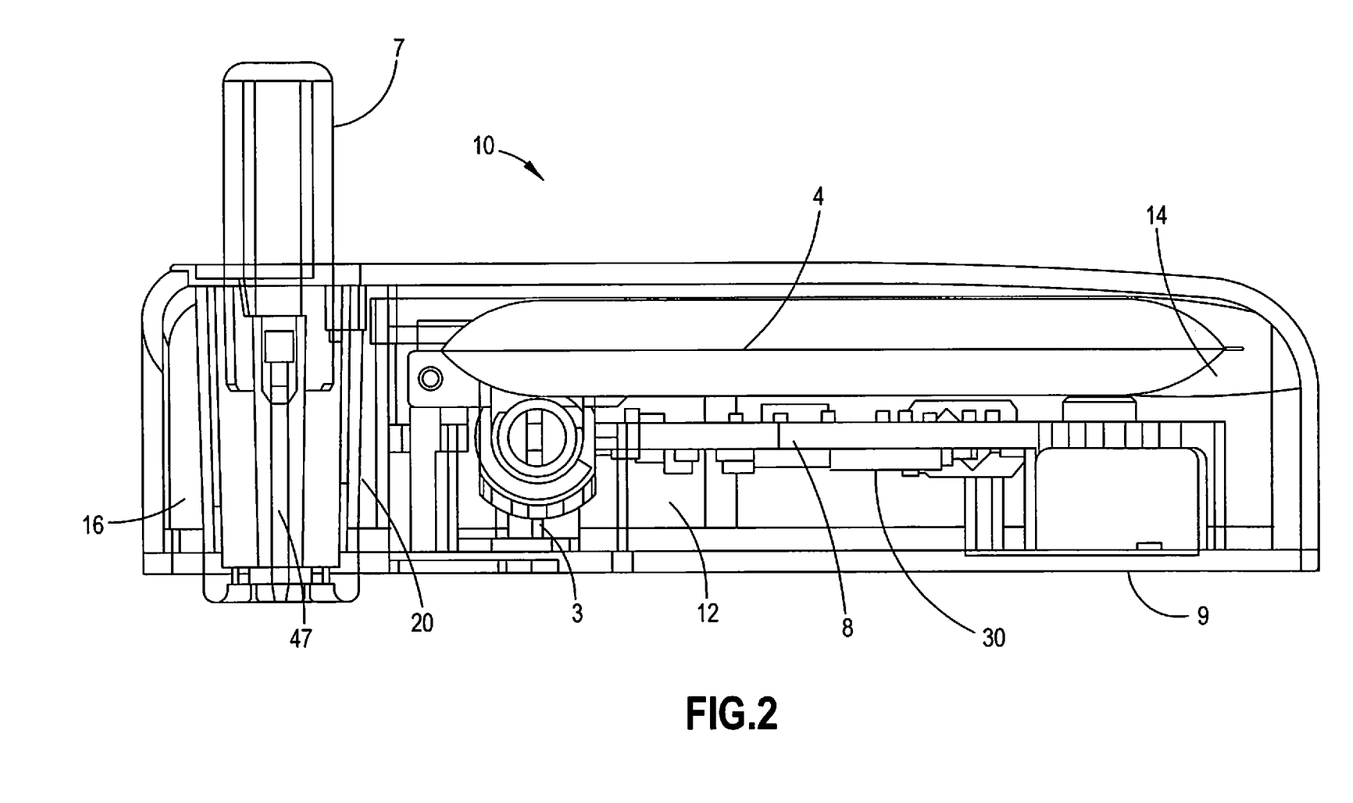
FIG. 2 is a cross-sectional view of FIG. 1 taken along line 2-2 of FIG. 1.

FIG. 2 is a cross-sectional view of the patch pump 1 illustrating various components. The main cover 2 and the base 9 define an interior 12 divided by a barrier 20 into a first internal region 14 and a second internal region 16. According to one embodiment, the patch pump 1 preferably includes a reservoir 4 for storing medicament (such as insulin), and a pump 3 for pumping the medicament to exit the reservoir 4. The patch pump 1 also preferably includes electronics 8 for programming and operating the patch pump 1, and an insertion mechanism 7 for inserting a cannula 47 into a skin of the patient to deliver medicament.

As previously noted, the interior 12 of the patch pump 1 is divided by the barrier 20 into the first internal region 14 and the second internal region 16. According to one embodiment, the barrier 20 is a part of the main cover 2. Preferably, the barrier 20 is integrally formed as a unitary structure with the main cover 2. The barrier 20 is preferably sealed to a protrusion on the base 9 such that the interface between the barrier 20 and the protrusion is hermetically joined using any of the processing methods described above or any other appropriate conventional sealing method. Alternatively, the interface between the barrier 20 and the protrusion can be liquid sealed. The barrier 20 separates the first internal region 14 from the second internal region 16 and protects the first internal region 14 from fluid ingress. According to one embodiment, the second internal region 16 is not sealed from fluid ingress.

The first internal region 14 includes components such as the pump 3 and the electronics 8. Examples of the electronics 8 include semiconductor chips, controllers, diodes, antennas, coils, batteries, discrete components (resistors and capacitors, for example) and circuit boards (such as a printed circuit board (PCB)) used to operate and control and operate the patch pump 1. As readily understood by the skilled artisan, it is desirable to have a dry environment for proper operation of these components, particularly the electronics 8. The second internal region 16 includes the insertion mechanism 7 and the cannula 47. According to one embodiment, because the insertion mechanism 7 interfaces with the skin of a patient, the second internal region 16 is neither a hermetically sealed environment, nor a liquid-tight environment.

According to one embodiment, the components of the first internal region 14 are different from the components of the second internal region 16. Alternatively, the first internal region 14 and the second internal region 16 share some of the same components. For example, in some embodiments, portions of the reservoir 4 are disposed in both the first and second internal regions 14, 16. When the reservoir and the insertion mechanism 7 are separated by the barrier 20, however, the two internal regions 14, 16 fluidly communicate for effective operation of the patch pump 1.

Figure 3:
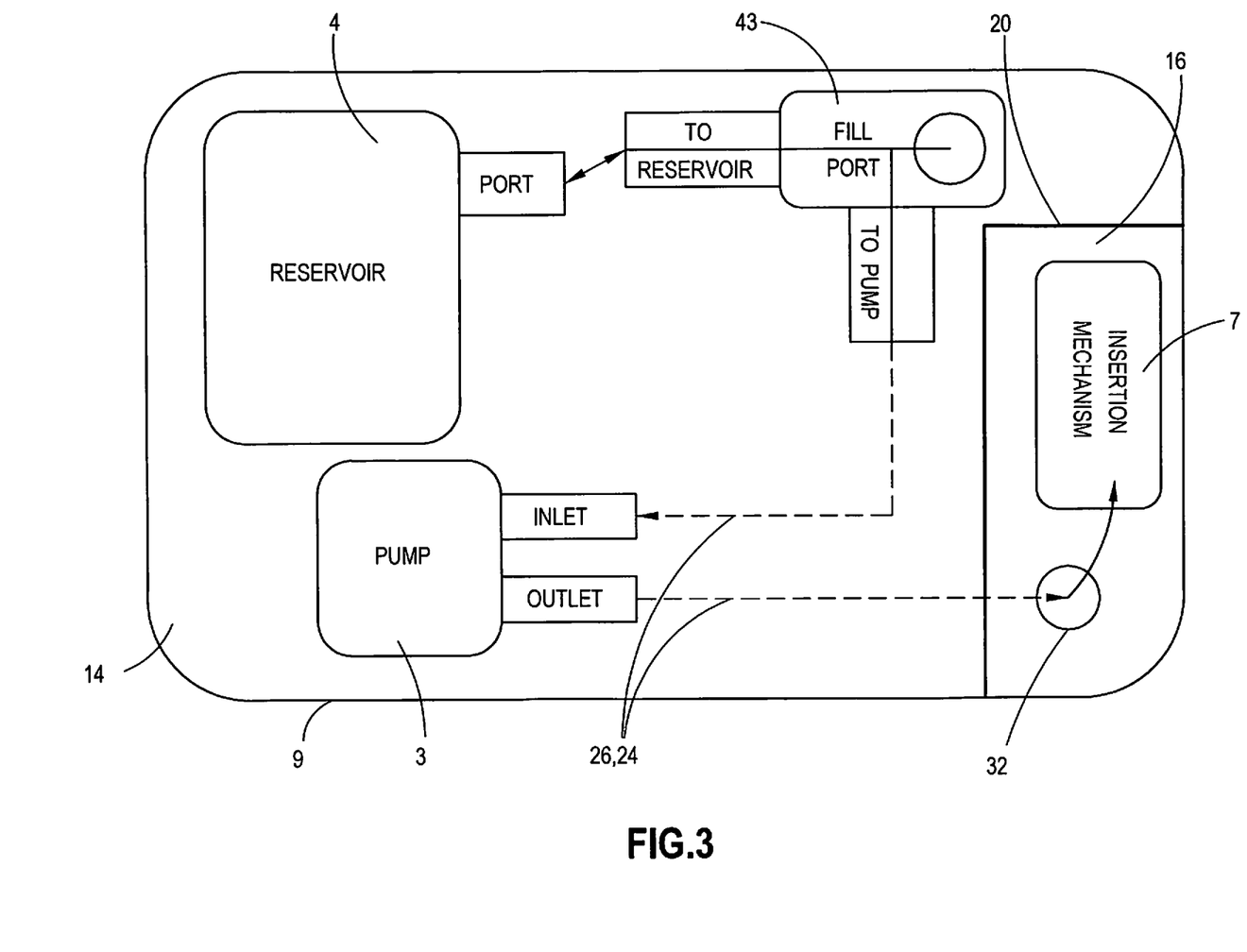
FIG. 3 is a schematic illustration of a medicament flow path of the patch pump of FIG. 1.

FIG. 3 is a schematic of an exemplary fluid path in the patch pump 1 in accordance with an illustrative embodiment of the present invention. Medicament enters the patch pump 1 via the fill port 43 to fill the reservoir 4. During operation of the patch pump 1, the pump 3 pulls medicament to exit the reservoir 4 into the fill port 43 via an auxiliary port, and subsequently flow to the inlet of the pump 3 via the second fluid channel 26. Next, the pump 3 drives the medicament to exit the pump 3, enter the first fluid channel 24, and flow to the receptacle 32 of the insertion mechanism 7. Finally, the insertion mechanism 7 receives the medicament from the receptacle 32 via tubing, for example, and delivers the medicament through the cannula 47 to the skin of the patient.

Figure 4:
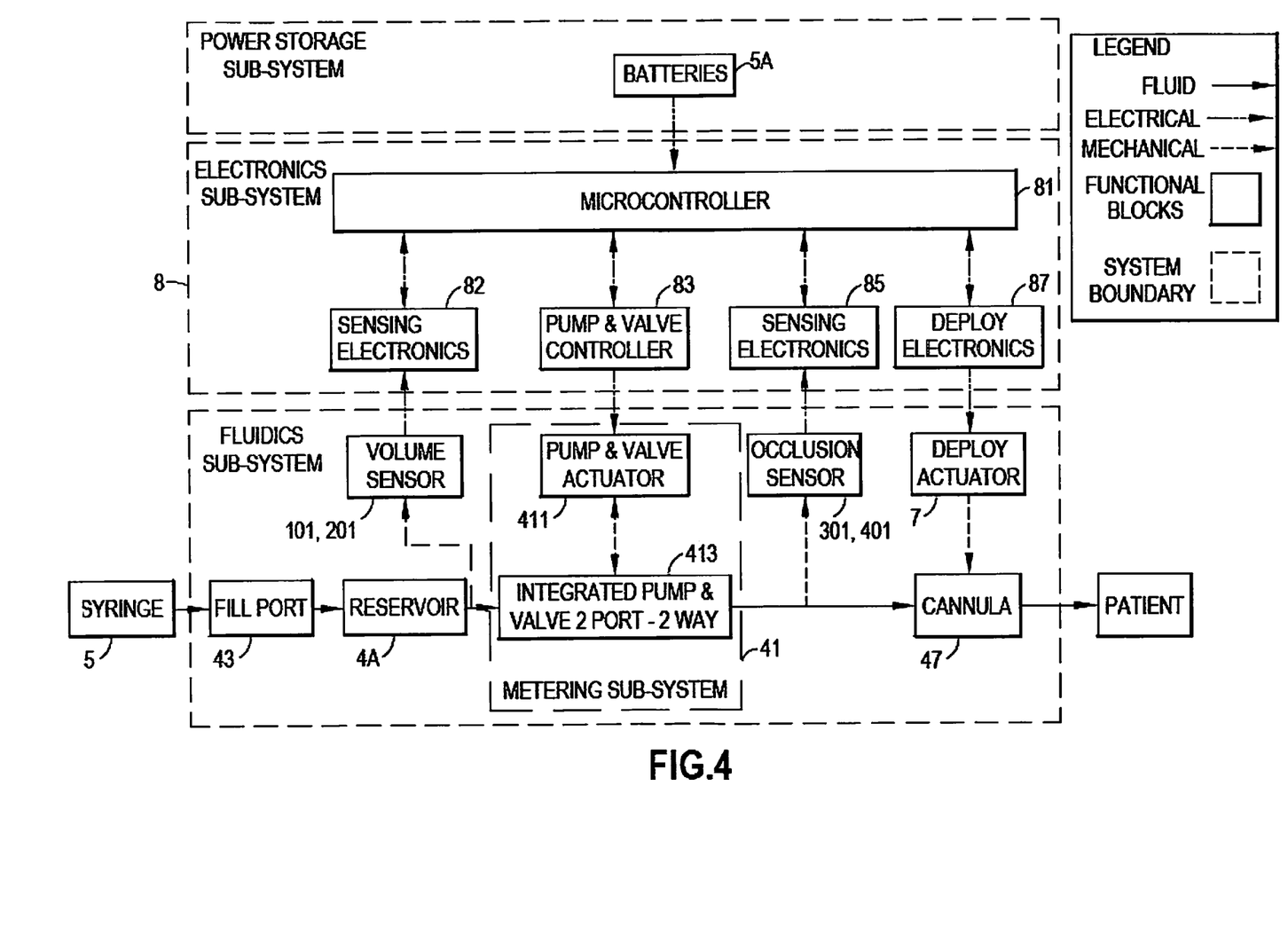
FIG. 4 is a block diagram depicting an illustrative implementation of a patch pump fluidic architecture and metering sub-system in accordance with an embodiment of the present invention.
Figure 5:
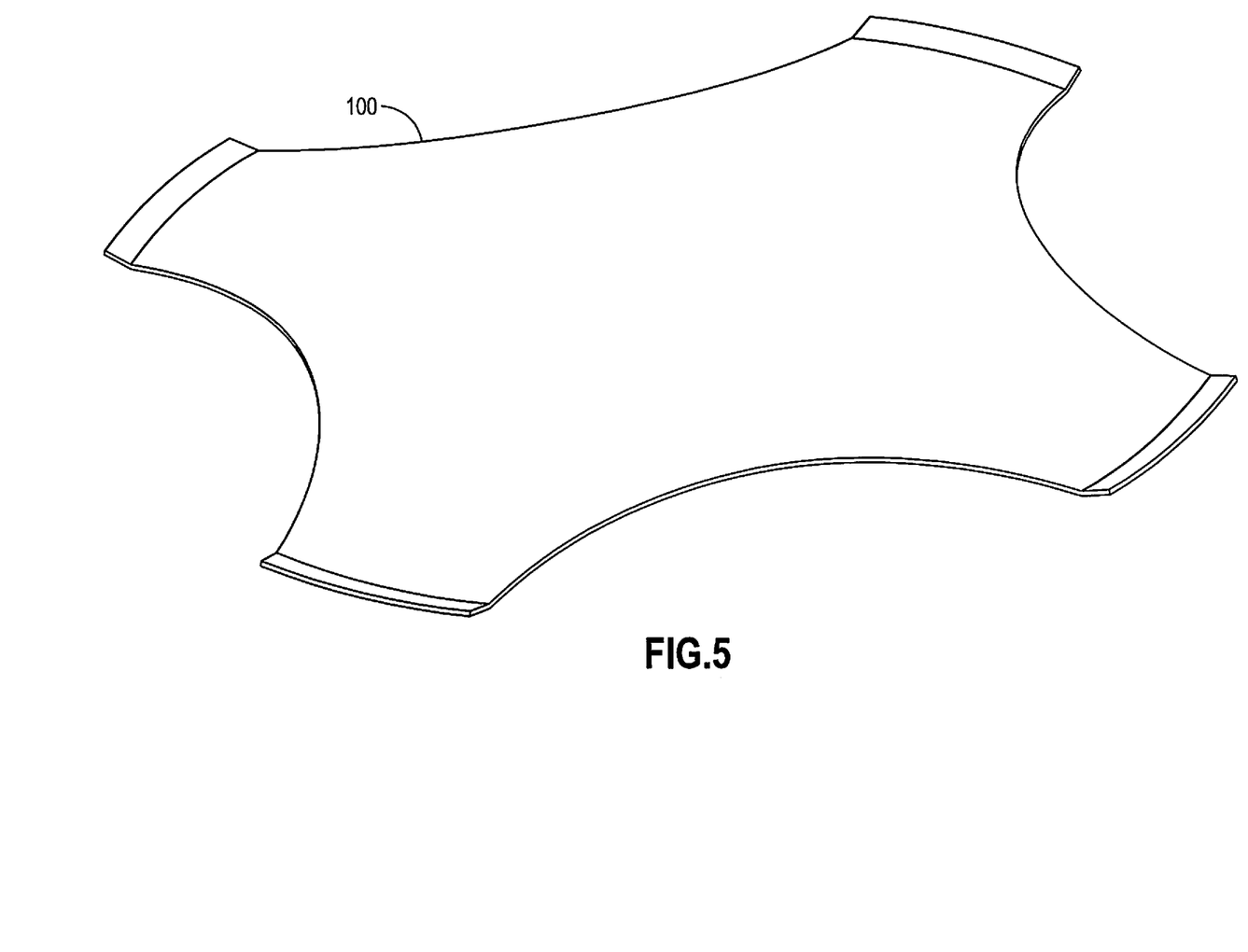
FIG. 5 is a perspective view of a bi-stable element or snap dome in accordance with and embodiment of the present invention.

FIG. 4 is an example patch pump fluidic architecture and metering sub-system diagram of the patch pump 1 of FIG. 1. A power storage sub-system for the patch pump 1 includes batteries 5A. The control electronics 8 of the patch pump 1 may include a microcontroller 81, sensing electronics 82, pump and valve controller 83, sensing electronics 85, and deployment electronics 87 that control the actuation of the patch pump 1. The patch pump 1A includes a fluidics sub-system that may include the reservoir 4, the reservoir fill port 43 for receiving a refill syringe 44 to refill the reservoir 4, and a low volume sensor 101, 201, as subsequently described. The fluidics sub-system may include a metering system 41 comprising a pump and valve actuator 411 and an integrated pump and valve mechanism 413. The fluidics sub-system may further include a deploy actuator 7, as well as the cannula 47 for insertion into an infusion site on the user's skin, and an occlusion sensor 301, 401, as subsequently described.

In some patch pumps, the volume sensor 48 for the reservoir 4 includes a piston with a plunger connected to a switch. When the low pressure is generated, the plunger is moved, thus triggering the switch. But such a sensor may encounter issues with stiction, a potentially high residual volume of medicament, and the need to deal with seals in the design and assembly of such a sensor. Such a sensor also requires many parts and many connections. Force sensing resistors in contact with the fluid path (either directly or indirectly) can also be employed. Force sensing resistors work well, but calibration, repeatability, and cost can be issues. Microelectromechanical systems (MEMS) can also be placed in contact with the fluid path. Although MEMS sensors are proven and reliable, they can be very expensive.

Figure 6:
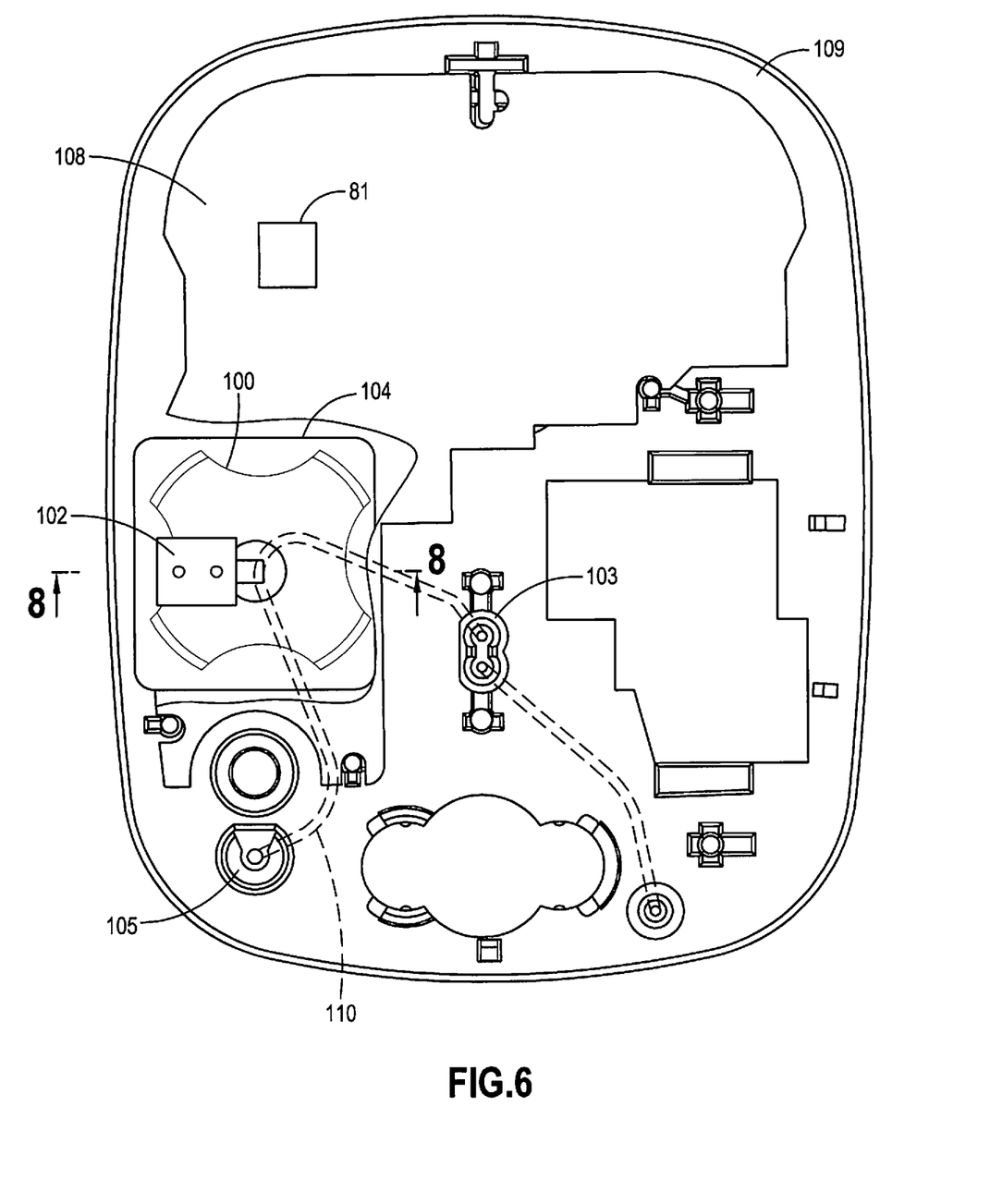
FIG. 6 is a plan view of the a base of a patch pump in accordance with an embodiment of the present invention with elements removed for clarity.
Figure 7:
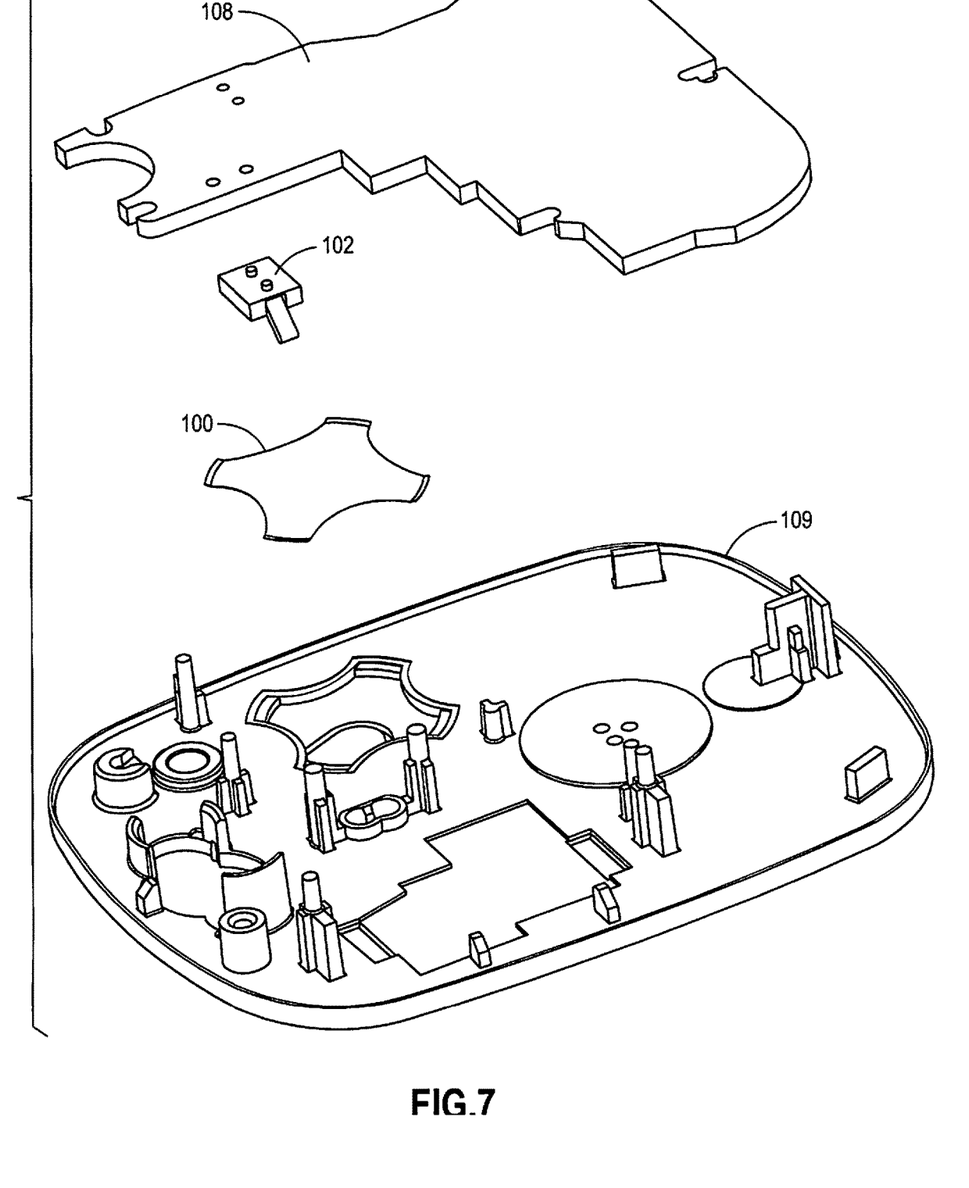
FIG. 7 is a perspective exploded view of the base of FIG. 6.

As shown in FIGS. 5-8, in accordance with an embodiment of the present invention, a bi-stable element or snap dome 100 can be employed with a switch 102 as a low volume sensor 101 for the reservoir 4. In FIG. 6, although the pump 3 and the reservoir 4 are not illustrated, the location of the pump connection point 103 of the pump 3 on the base 109 and the reservoir connection point 105 of the reservoir 4 on the base 109 are illustrated. The fluid path 110 fluidly connects the reservoir 4 and the pump 3. According to one embodiment, the fluid path 110 is a recess in the base 109 that is covered by a pressure sensitive adhesive or a membrane or film 104 that fluidly seals the recess to form the fluid path 110.

As shown in FIG. 6, a portion of the fluid path 110 travels beneath the snap dome 100 so that the snap dome 100 is in fluid communication with the fluid path 110. According to one embodiment, the snap dome 100 and this portion of the fluid path 110 are covered by a pressure sensitive adhesive or film 104, such as Mylar, that can fluidly seal the portion of the fluid path 110. In this embodiment, the snap dome 100 is disposed within the fluid path 110.

According to one embodiment, the pump 3 is a positive displacement pump. For every stroke, a known amount of fluid is pulled from the reservoir. According to one embodiment, with every stroke, the pump pulls 5 microliters from the reservoir 4. According to one embodiment, the reservoir 4 is a soft, self-collapsing reservoir 4, thereby mimizing the pressure required to pull liquid from the reservoir, permitting use of a small pump 3, and avoiding high pressures in the fluid path 110.

Figure 8:
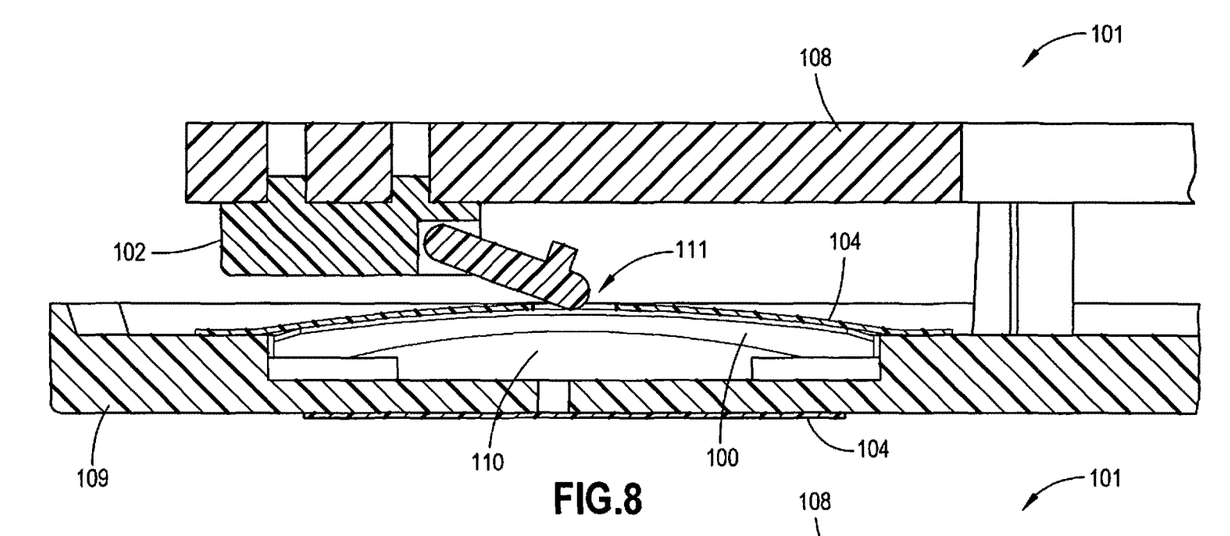
FIG. 8 is a partial cross-sectional view of the base of FIG. 6 taken along line 8-8 with the snap dome of FIG. 5 in a first stable position.

As best shown in FIG. 8, when the reservoir 4 is full, the switch 102 is in contact with the snap dome 100, which is in an upward-arched, first stable position. Once the reservoir 4 is nearly empty, the pumping of the pump 3 reduces the pressure within the fluid path 110. The snap dome 100 is configured to snap out of contact with the switch 102 (see FIG. 9) into a second stable position once the pressure within or beneath the snap dome 100 (within the fluid path 110) decreases below a predetermined pressure. In other words, with the snap dome 100 being in the fluid path, when the reservoir is full, there is a substantially consistent negative pressure or vacuum (within a predetermined variance) as the pump 3 pulls the fluid from the reservoir 4 along the fluid path 110 and underneath the snap dome 100. But as the reservoir 4 nears emptiness, the continued pumping of the pump 3 along with a reduced amount of fluid produces a greater negative pressure. With sufficient negative pressure, the snap dome 100 is pulled down by the negative pressure to the second stable position, and out of contact with the switch 102 (see FIG. 9).

Figure 9:
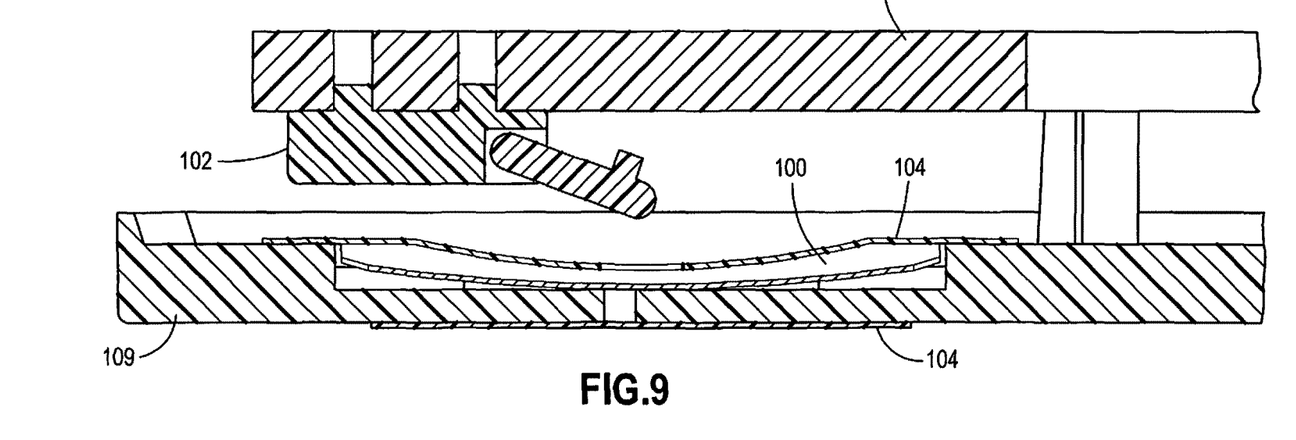
FIG. 9 is a partial cross-sectional view of the base of FIG. 6 taken along line 8-8 with the snap dome of FIG. 5 in a second stable position.

Put another way, because the snap dome 100 is interacting with the fluid path 110 (as it is part of the fluid path 110), when a predetermined negative pressure is achieved because every stroke of the pump 3 is pulling more and more of a vacuum when the reservoir 4 is nearly empty, the vacuum pulls the snap dome 100 out of contact with the switch 102, and the snap dome 100 moves to its second stable position (FIG. 9).

According to one embodiment, the second stable position of the snap dome 100 is a downward-arched position. According to another embodiment, the second stable position of the snap dome 100 is substantially flat. According to another embodiment, the second stable position of the snap dome 100 is upwardly-arched, but less so than the first stable position.

Material choices for the snap dome 100 include stainless steel, beryllium, copper, other metal alloys, or plastic, such as acrylonitrile butadiene styrene (ABS), cyclic olefin copolymer (COP), or polypropylene. Ideally, the snap dome should be sufficiently resilient to be able to snap back to its original stable position. The required thickness of a given material to provide the desired resilience is a factor in material selection, particularly when trying to minimize the size of the snap dome. Another factor is the required force to actuate the snap dome 100, because actuation induced by vibration is undesirable, and because this factor is interactive with the size and performance of the pump 3. Consistency (to reduce false actuation) is also desirable. Experiments have determined an acceptable balance of size and performance can be achieved with a 14 mm stainless steel snap dome (i.e., the snap dome can be circumscribed by a 14 mm diameter circle).

The switch 102 can be a mechanical switch, such as an SPVR switch from ALPS. Alternatively, the switch 102 can be an electrical switch. For example, if an electrically conductive material is chosen for the snap dome 100, then the film 104 covering the snap dome 100 and the portion of the fluid path 110 beneath the snap dome 100 can have an opening 111 therein to provide electrical contact between the snap dome 100 and the switch 102. When the snap dome actuates, the electrical contact is broken. Alternatively, the film 104 can be electrically conductive. As yet another alternative, an electrically conductive pad can be disposed on the film 104 so that there is no opening in the film 104, and when the snap dome 100 actuates, the electrical contact between the electrically conductive pad 113 (See FIG. 11) and the switch 102 is broken.

Once the switch 102 is triggered by actuation of the snap dome 100, a variety of indications can be given to the user by the controller 81 to let the user know that delivery of the medicament is complete, for example, a sound and/or vibration, or a text display. The triggering of the switch can be a signal to the controller 81 to stop the pump 3. Alternatively, once the switch is triggered, the controller 81 can control the pump 3 to continue pumping for a predetermined amount of time, because the approximate volume remaining in the reservoir would be known, as well as the approximate amount the pump draws with each cycle. Triggering of the switch 102 can also be used as a signal to the controller 81 to withdraw an injection needle.

Figure 10:
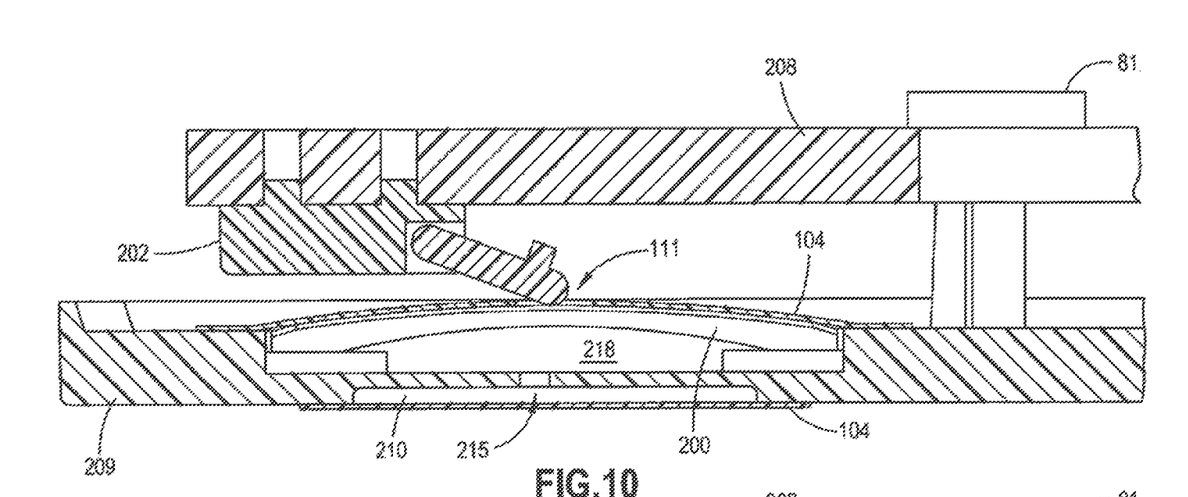
FIG. 10 is a partial cross-sectional view in accordance with another embodiment of the present invention.

In another embodiment shown in FIG. 10, a snap dome 200 can be employed with a switch 202 as a low volume sensor 201. In this embodiment, the snap dome 200 does not reside within the fluid path 210, but instead, the base 209 has an opening or hole 215 therein through which the fluid path communicates with the space 218 beneath the snap dome. The hole 215 is sized so that pressure can equilibrate between the fluid path 210 and the space 218 beneath the snap dome 200, but the surface tension of the medicament in the fluid path 210 prevents the medicament from flowing through the hole 215.

In such an embodiment, as with the previously described embodiment, with the snap dome 200 being in fluid communication with the fluid path 210 via the hole 215 to equilibrate pressure therebetween, as the reservoir 4 nears emptiness, the continued pumping of the pump 3 along with a reduced amount of fluid produces a greater negative pressure in the fluid path 210 and the space 218 beneath the snap dome 200. With sufficient negative pressure, the snap dome 200 is actuated by the negative pressure and displaces out of contact with the switch 202.

Figure 11:
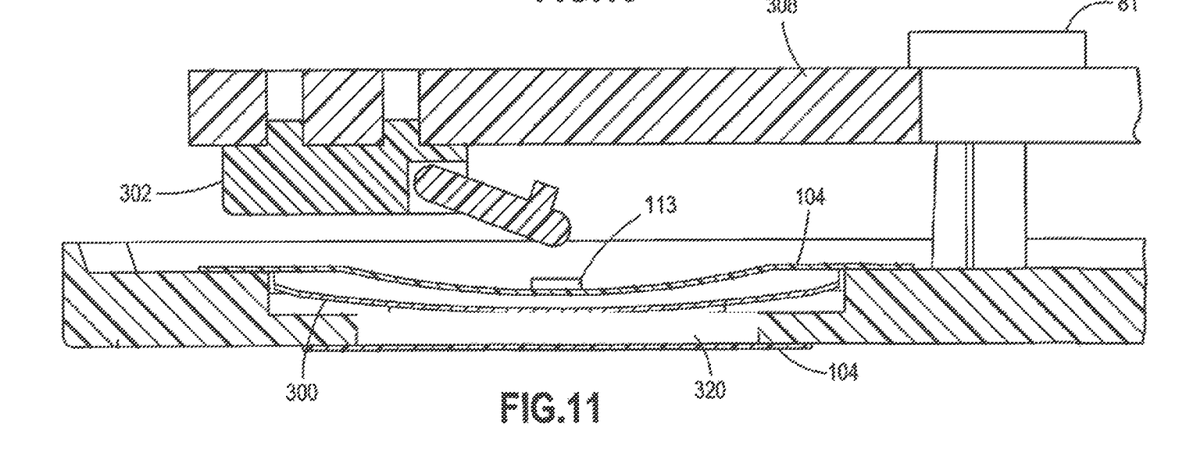
FIG. 11 is a partial cross-sectional view in accordance with another embodiment of the present invention.

In another embodiment shown in FIG. 11, in addition to or instead of the snap dome 100 or 200 being employed as a low volume sensor, a snap dome 300 can be employed with a switch 302 as an occlusion sensor 301. In this embodiment, a downstream fluid path 320 connects the pump 3 and the delivery cannula 47. The snap dome 300 is disposed in fluid communication with the downstream fluid path 320, and out of contact with a switch 302. In this embodiment, the snap dome 300 is inverted i.e., the snap dome is disposed to arch downwardly, and is in fluid contact with the downstream fluid path 320. In this embodiment, the combination of the snap dome 300 and the switch 302 serve as an occlusion detector. For example, if an occlusion occurs in the downstream fluid path 320, as the pump 3 continues to pump medicament, the pressure in the downstream fluid path 320 increases. Once the pressure increases to a predetermined threshold, the inverted snap dome 300 actuates and snaps into contact with the switch 302. This switch triggering can be used by the controller 81 as detection of an occlusion.

Figure 12:
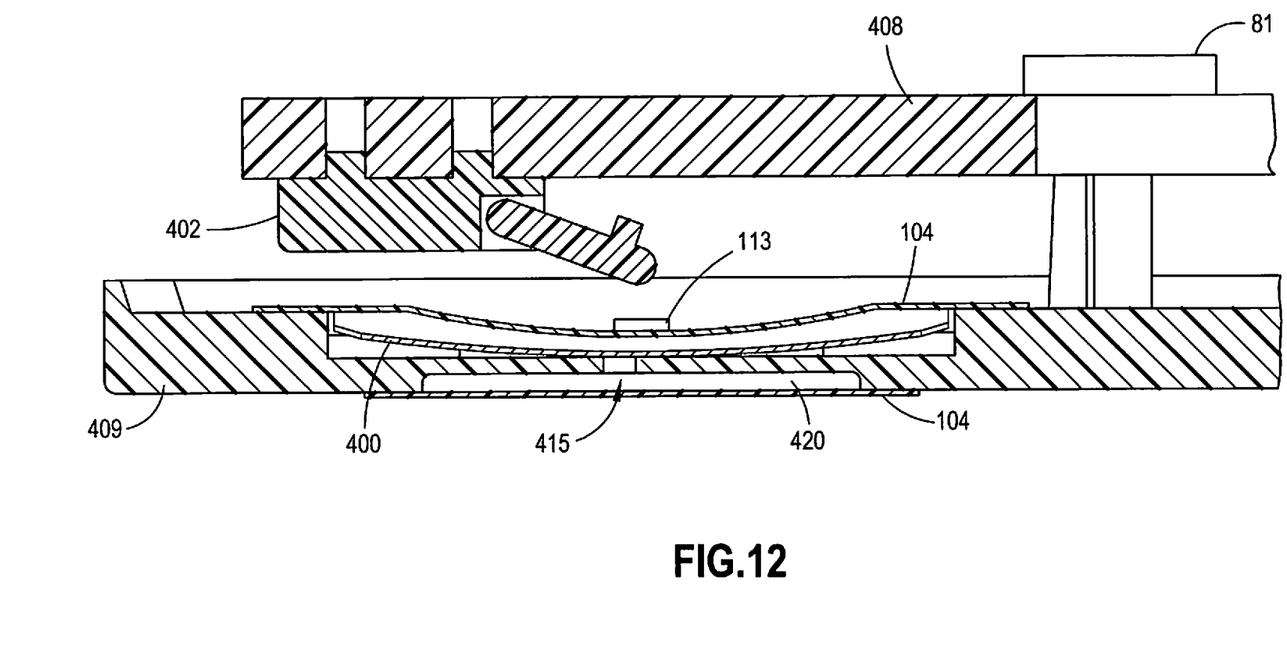
FIG. 12 is a partial cross-sectional view in accordance with another embodiment of the present invention.

As with previously described alternative embodiments, as shown in FIG. 12 a snap dome 400 can be employed with a switch 302 as an occlusion sensor 401. In this embodiment, the base 409 could have a hole 415 therein in fluid communication with the downstream fluid path 420. The hole 415 is sized so that pressure can equilibrate between the downstream fluid path 420 and the space 418 beneath the snap dome 400, but the surface tension of the medicament in the downstream fluid path 420 prevents the medicament from flowing through the hole 415.

As an alternative occlusion sensor, the switch 302, 402 could be disposed within the downstream fluid path 320, 420 and in contact with the snap dome 300, 400 in its initial state, and once the snap dome is actuated by the predetermined increased pressure, the snap dome 300, 400 snaps out of contact with the switch 302, 402.

Embodiments of the present invention include a snap dome (typically metal, but could also be plastic, or a bistable material or a membrane that flexes at certain pressure) attached and sealed to the fluid path to snap when the medicament reservoir is empty. This snap is to be designed and controlled such that it occurs at a reasonable negative pressure. The dome switch is attached and sealed to the fluid path with either a pressure sensitive adhesive or with any other film that is permanently welded and sealed to the fluid path. The attachment does not constrain the ends of the snap dome, so that the film does not affect the snap dome's functionality. A switch may be located in contact with the un-deflected (untriggered or unactuated) snap dome such that when the snap dome is triggered, the switch is activated. The switch may be normally closed and then open or vice-versa. The dome may be sealed to the fluid path in such a way that the top of the dome, if metal, is exposed, thus allowing the use of simple mechanical contacts to close a circuit that then opens when the dome is activated and pulls away. Alternatively the seal material can be coated with conductive material or may be conductive.

These embodiments are an inexpensive option for detecting low/empty volume in the reservoir. Particularly when used with simple mechanical contacts and a conductive cover/top, these embodiments achieve their lowest cost. The cost of a snap dome is very low but the functionality is very repeatable.

Although only a few embodiments of the present invention have been shown and described, the present invention is not limited to the described embodiments. It will be appreciated by those skilled in the art that other changes may also be made to the disclosed embodiments without departing from the scope of the invention. In addition, any of the embodiments, features and/or elements disclosed herein may be combined with one another to form various additional combinations not specifically disclosed, as long as the embodiments, features and/or elements being combined do not contradict each other. All such changes and combinations are considered to be within the scope of the invention as defined by the appended claims and their equivalents.

What is claimed is:

1. A low medicament sensor for a medicament delivery device having a reservoir, a pump, and a fluid path therebetween for medicament, the sensor comprising:
a switch; and
a snap dome that is:
   initially in contact with the switch;
   in fluid communication with the fluid path; and
   configured to snap out of contact with the switch when a pressure within the snap dome decreases below a predetermined pressure;
wherein:
   the device further comprises a base having a hole therein that is in fluid communication with the fluid path;
   the snap dome is disposed on the base over the hole; and
   the hole is sized:
      to equilibrate pressure between the fluid path and a space within the snap dome; and
      so that surface tension of the medicament prevents medicament flow therethrough.

2. The sensor according to claim 1, wherein the snap dome is disposed within the fluid path.

3. The sensor according to claim 1, wherein the switch comprises a mechanical switch in communication with a controller of the device.

4. The sensor according to claim 1, wherein:
the switch comprises an electrical switch in communication with a controller of the device; and
the snap dome comprises conductive metal.

5. The sensor according to claim 4, wherein the conductive metal comprises one of stainless steel, copper, beryllium, or a metal alloy.

6. The sensor according to claim 1, wherein:
the switch comprises an electrical switch in communication with a controller of the device;
the snap dome is disposed within the fluid path; and
the snap dome is sealed to the fluid path with an electrically conductive membrane to provide electrical contact of the snap dome with the electrical switch.

7. A low medicament sensor for a medicament delivery device having a reservoir, a pump, and a fluid path therebetween for medicament, the sensor comprising:
a switch; and
a snap dome that is:
   initially in contact with the switch;
   in fluid communication with the fluid path; and
   configured to snap out of contact with the switch when a pressure within the snap dome decreases below a predetermined pressure;
wherein:
   the snap dome comprises conductive metal;
   the snap dome is disposed within the fluid path;
   the snap dome is sealed to the fluid path with a membrane; and
   an outer portion of the snap dome is not covered by the membrane to provide electrical contact of the snap dome with the switch.

8. A medicament delivery device, comprising:
a reservoir for storing medicament;
a pump;
a fluid path for the medicament fluidly connecting the reservoir and the pump;
a switch;

a snap dome that is:
  initially in contact with the switch;
  in fluid communication with the fluid path; and
  configured to snap out of contact with the switch when a pressure within the snap dome decreases below a predetermined pressure;
a base having a hole therein that is in fluid communication with the fluid path;
wherein the snap dome is disposed on the base over the hole; and
the hole is sized:
  to equilibrate pressure between the fluid path and a space within the snap dome; and
  so that surface tension of the medicament prevents medicament flow therethrough.

9. The device according to claim 8, wherein the snap dome is disposed within the fluid path.

10. The device according to claim 8, further comprising:
a controller;
wherein the switch comprises a mechanical switch in communication with the controller.

11. The device according to claim 8, further comprising:
a controller, wherein:
the switch comprises an electrical switch in communication with the controller; and
the snap dome comprises conductive metal.

12. The device according to claim 11, wherein the conductive metal comprises one of stainless steel, copper, beryllium, or a metal alloy.

13. The device according to claim 8, wherein:
the switch comprises an electrical switch in communication with a controller of the device;
the snap dome is disposed within the fluid path; and
the snap dome is sealed to the fluid path with an electrically conductive membrane to provide electrical contact of the snap dome with the electrical switch.

14. A medicament delivery device, comprising:
a reservoir for storing medicament;
a pump;
a fluid path for the medicament fluidly connecting the reservoir and the pump;
a switch; and
a snap dome that is:
  initially in contact with the switch;
  in fluid communication with the fluid path; and
  configured to snap out of contact with the switch when a pressure within the snap dome decreases below a predetermined pressure;
wherein:
  the snap dome comprises conductive metal;
  the snap dome is disposed within the fluid path;
  the snap dome is sealed to the fluid path with a membrane; and
  an outer portion of the snap dome is not covered by the membrane to provide electrical contact of the snap dome with the switch.

15. A medicament delivery device, comprising:
a reservoir for storing medicament;
a pump;
a fluid path for the medicament fluidly connecting the reservoir and the pump;
a switch;
a snap dome that is:
  initially in contact with the switch;
  in fluid communication with the fluid path; and
  configured to snap out of contact with the switch when a pressure within the snap dome decreases below a predetermined pressure;
a medicament delivery cannula;
a medicament delivery fluid path disposed between the pump and the cannula; and
an occlusion sensor, comprising:
  a second switch; and
  a second snap dome that is:
    initially out of contact with the second switch;
    in fluid communication with the medicament delivery fluid path; and
    configured to snap into contact with the second switch when a pressure in the medicament delivery fluid path increases above a predetermined pressure.

16. The device according to claim 15, further comprising:
a base having a hole therein that is in fluid communication with the medicament delivery fluid path;
wherein the second snap dome is disposed on the base over the hole; and
the hole is sized:
  to equilibrate pressure between the medicament delivery fluid path and a space around the second snap dome; and
  so that surface tension of the medicament prevents medicament flow therethrough.

* * * * *